United States Patent [19]

Cama et al.

[11] 4,123,528

[45] Oct. 31, 1978

[54] 3-(SUBSTITUTED THIO) CEPHALOSPORINS, DERIVATIVES AND NUCLEAR ANALOGUES THEREOF

[75] Inventors: Lovji D. Cama, Edison; Burton G. Christensen, Scotch Plains, both of N.J.

[73] Assignee: Merck & Co., Inc., Rahway, N.J.

[21] Appl. No.: 819,652

[22] Filed: Jul. 27, 1977

Related U.S. Application Data

[63] Continuation of Ser. No. 634,081, Nov. 21, 1975, abandoned.

[51] Int. Cl.$^2$ ............... C07D 498/04; A61K 31/535
[52] U.S. Cl. ............................. 424/248.52; 544/26; 544/90; 424/246
[58] Field of Search ............... 544/90, 26; 424/248.52

[56] References Cited

U.S. PATENT DOCUMENTS 3,992,377  11/1976  Chauvette et al. ................. 544/26

FOREIGN PATENT DOCUMENTS 2,537,974  3/1976  Fed. Rep. of Germany ............. 544/26

OTHER PUBLICATIONS

Chemical Abstracts, vol. 81, abst. 37560f (1974) (abst. of Ger. Offen. 2,355,209).

*Primary Examiner*—John D. Randolph
*Attorney, Agent, or Firm*—Frank M. Mahon; James A. Arno; Julian S. Levitt

[57] ABSTRACT

Disclosed is a class of cephalosporins including the carba, aza and oxa nuclear analogues thereof which bear at the 3-position a substituted thio substituent; such compounds are useful as antibiotics. Also disclosed are processes for the preparation of such compounds; pharmaceutical compositions comprising such compounds; and methods of treatment comprising administering such compounds and compositions when an antibiotic effect is indicated.

3 Claims, No Drawings

3-(SUBSTITUTED THIO) CEPHALOSPORINS, DERIVATIVES AND NUCLEAR ANALOGUES THEREOF

This is a continuation of application Ser. No. 634,081 filed Nov. 21, 1975 now abandoned.

BACKGROUND OF THE INVENTION

This invention relates to a novel class of cephalosporins and analogues thereof and the pharmaceutically acceptable salt, ester, and amide derivatives thereof which bear in the 3-position of the 6-membered ring a substituted thio substituent. These compounds are useful as antibiotics. This invention also relates to processes for preparing such compounds; pharmaceutical compositions comprising such compounds; and methods of treatment comprising administering such compounds and compositions when an antibiotic effect is indicated.

The novel class of cephalosporins and analogues thereof to which this invention relates may be generically represented by the following structural formula:

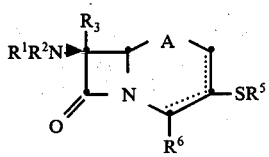

I wherein
the dotted line indicates provision for both $\Delta^2$ and $\Delta^3$ embodiments;
A is S, O, SO, $CH_2$, or $NR^7$, ($R^7$ is selected from the group consisting of hydrogen, alkyl, formyl, acyl, thioacyl, alkylsulfonyl, and aryl sulfonyl);
$R^1$ and $R^2$ are independently selected from the group consisting of hydrogen or an acyl group. The term acyl is by definition those acyl radicals conventionally known in the cephalosporin and penicillin art and includes thio analogues thereof wherein the carbonyl oxygen is replaced by sulphur and diacyl radicals wherein $R^1$ and $R^2$ are joined together.
$R^3$ is selected from the group consisting of hydrogen, alkoxy, alkylthio, halogen such as fluoro and bromo;
$R^5$ is selected from the group consisting of hydrogen; substituted and unsubstituted: alkyl; aryl, aralkyl, heteroaryl and heteroaralkyl wherein the heterocyclic moiety comprises 4–6 ring atoms and the hetero atom (or atoms) is O, N or S; wherein the ring or chain substituent is selected from: amino, carboxy, hydroxy alkoxy, carbalkoxy, lower alkyl, heteroaryl, and substituted amino such as mono- and di-alkylamino, acylamino; examples of such substituents, $R^5$ are: β-aminoethyl, β-hydroxyethyl, phenyl, substituted phenyl, benzyl, phenethyl and the like; and
$R^6$ is selected from the group consisting of $PO(OH)_2$, $SO_2(OH)$, $SO_2NH_2$ and derivatives thereof and $COXR^8$ wherein X is oxygen or sulphur and $R^8$, is inter alia, representatively selected from the group consisting of trialkylsilyl, and the pharmaceutically acceptable salt, ester and amide moieties known in the antibiotic bicyclic β-lactam art such as sodium, potassium, pivaloyloxymethyl, and the like.

There is a continuing need for new antibiotics. For, unfortunately, there is no static effectiveness of a given antibiotic because continued wide scale usage of any such antibiotic selectively gives rise to strains of pathogens which are resistant to the exploited antibiotic. In addition, the known antibiotics suffer from the disadvantage that they are effective only against certain types of microorganisms. Accordingly, the search for new antibiotics has continued.

Unexpectedly, it has been discovered that the compounds of the present invention are broad spectrum antibiotics; which are useful in animal and human therapy and in inanimate systems. It will be recognized from the above generic representation (I) that the principal novel feature of the compounds of the present invention is the substituent at the 3-position, a substituted thio radical. It will also be noted, except where expressly stated, that the balance of the cephalosporin or cephalosporin-like structure (I) is well-known in the relevant art.

Thus, it is an object of the present invention to provide a novel class of antibiotics which includes, inter alia, species having the basic nuclear structure of the cephalosporins but which are characterized by having a substituted thio radical at the three-position. These antibiotics are active against a broad range of pathogens, which representatively include gram positive bacteria such as Staphylococcus aureus, Streptococcus pyogenes, and gram negative bacteria such as E. coli and Salmonella typhimurium, Proteus mirabilis, and Proteus morganii. Further objects of this invention are to provide chemical processes for the preparation of such antibiotics; intermediates useful in preparing such antibiotics; pharmaceutical compositions comprising such antibiotics; and to provide methods of treatment comprising administering such antibiotics and compositions when an antibiotic effect is indicated.

DETAILED DESCRIPTION OF THE INVENTION

The following U.S. Patents and co-pending, commonly assigned U.S. Patent Applications are incorporated herein by reference for the subject matter which they disclose as it relates to the preparation of necessary starting materials needed for a description of the present invention. It will be noted that these patents and applications disclose the basic nucleus (II) (and derivatives thereof) upon which the present invention relies:

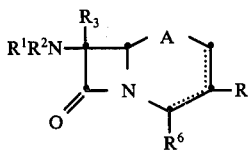

II wherein all substituents, except R, are as previously defined; and R is selected from the group consisting of hydrogen, acyloxymethyl such as acetoxymethyl and carbamoyloxymethyl, for example. The incorporated-by-reference materials are: commonly assigned, South African Pat. No. 73/8503.

With reference to structure I, above-given, the preferred embodiments of the present invention are those wherein:
A is selected from S, $CH_2$, SO, and O;
$R^3$ is selected from hydrogen, methoxyl, and lower alkyl thio.
$R^5$ is hydrogen formyl or $-(CH_2)_n-Y$ wherein Y is hydrogen, hydroxyl, halo, mercapto, acyloxy, acylthio, substituted hydroxy, substituted mercapto, a quaternary ammonium group, azido, amino, carboxy and carbalkoxy, or an N-substituted amino group; and n is an integer from 1 to 6 and preferably 1 to 3. Thus, $(CH_2)_n$—Y can be haloalkyl, such as chloromethyl, bromomethyl or fluoroethyl.

When Y is a substituted hydroxy or substituted mercapto group, $R^5$ can be shown by the formula

—(CH$_2$)$_n$ZR' where Z is oxygen or sulfur, and R' is an acyl group; a straight chain or branched chain loweralkyl, alkenyl or alkynyl group; an aryl group; an aralkyl group; or a heterocyclic group such as heteroaryl or heteroalkyl. These groups can be unsubstituted or can be substituted by radicals such as alkyl, alkoxy, halo, cyano, carboxy, carbamoyl, azido, sulfo, amino, substituted amino, haloalkyl, carboxyalkyl, carbamoylalkyl, N-substituted carbamoylalkyl, guanidino, N-substituted guanidino, guanidoalkyl, sulfamyl, substituted sulfamyl, and the like. Representative of the groups thus represented that might be mentioned are methoxymethyl, n-propoxymethyl, methylthiomethyl, acetoxymethyl, propionyloxymethyl, benzoyloxymethyl, (p-chlorobenzoyl)oxymethyl, (p-methylbenzoyl)oxymethyl, pivaloyloxymethyl, (1-adamantyl)carboxymethyl, butanoyloxymethyl, carbamoyloxymethyl, (N-methylcarbamoyl)oxymethyl, (N-ethylcarbamoyl)oxymethyl, [N-(2-chloroethyl)carbamoyl]oxymethyl, (N-phenylcarbamoyl)oxymethyl, (n-p-sulfophenylcarbamoyl)oxymethyl, p-carboxymethylphenylcarbamoyloxymethyl, methoxycarbonyloxymethyl, isobutanoyloxymethyl, cyclobutylcarbonyloxymethyl, carbamoylthiomethyl, (ethoxythiocarbonyl)thiomethyl, (n-propoxythiocarbonyl)thiomethyl, (cyclopentanoxythiocarbonyl)thiomethyl, methylthiomethyl, N,N-diethylthiocarbamoylthiomethyl, N-methylpiperazinium-1-thiocarbonylthiomethyl, N,N-dimethylpiperazinium-1-thiocarbonylthiomethyl, 2-furoylthiomethyl, isothiouroniummethyl, (5-methyl-1,3,4-thiadiazol-2-yl)thiomethyl, p-tolylsulfonylthiomethyl, mesyloxymethyl, 1-methyl-1,2,3,4-tetrazolyl-5-thiomethyl, tosyloxymethyl, sulfamoyloxymethyl, 1-naphthoyloxymethyl, 2-furylacetoxymethyl, cinnamoyloxymethyl, p-hydroxycinnamoyloxymethyl, p-sulfocinnamoyloxymethyl and 1R:2S-epoxypropylphosphonyloxymethyl.

The substituent $(CH_2)_n$Y can also be a group of the general formula:

$(CH_2)_nY_1$ wherein $Y_1$ represents amino or substituted amino including nitrogen heterocycles and substituted heterocyclic groups. Examples of such groups that might be mentioned are aminomethyl, acetamidomethyl, carbamoylaminomethyl, N,N-dimethylaminomethyl, N-(2-chloroethyl)aminomethyl, 5-cyanotriazol-1-ylmethyl, 4-methoxycarbonyltriazol-1-ylmethyl.

Representative of the quaternary ammonium groups representing Y that might be mentioned are pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxymethyl)pyridinium, 4-(hydroxymethyl)pyridinium, 4-(trifluoromethyl)pyridinium, quinolinium, picolinium and lutidinium.

The preferred groups representing Y are hydrogen, halo, azido, cyano, hydroxy, alkoxy, aryloxy, aralkyloxy, heterocycleoxy, mercapto, alkylthio, arylthio, aralkylthio, heterocyclethio, amino, alkylamino, alkanoylamino, hydroxyphenyl, acylthio, acyloxy, isothiouronium, sulfamoyloxy, quaternary ammonium, a heterocyclic tertiary amine, alkylsulfonyloxy and (cis-1,2-epoxypropyl)phosphono. The heterocycles can be a 5- or 6-membered hetero ring containing one or more nitrogen, oxygen or sulfur atoms. The acyl group can be a loweralkanoyl group of 2–6 carbon atoms, carbamoyl, or thiocarbamoyl and N-alkyl or N,N-dialkyl derivatives thereof. The alkyl group of the foregoing substituents contains 1–6 carbon atoms and may be further substituted radicals such as alkoxy, halo, amino, cyano, carboxy, sulfo, and the like.

$R^1$ and $R^2$ are selected from hydrogen, acyl, or $R^1$ and $R^2$ may be joined to form a N,N-diacyl. The acyl radical represented by either $R^1$ or $R^2$ can be a substituted or unsubstituted aliphatic, aromatic or heterocyclic, arlaiphatic or heterocylylaliphatic carboxylic acid radical or a carbothioic acid radical such as the acyl radicals of the known cephalosporins and penicillins. These acyl radicals can be represented by the general formula:

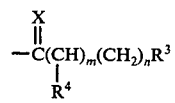
$$-\overset{X}{\underset{R^4}{\overset{\|}{C}}}(CH)_m(CH_2)_nR^3$$

wherein X is oxygen or sulphur, $R^4$ is a radical of the group defined below, $m$ and $n$ represent 0–4 and $R^3$ represents R" or ZR", which are defined below.

One group of acyl radicals can be represented by the general formula

$$-\overset{X}{\overset{\|}{C}}-R''$$

wherein R" represents a substituted or unsubstituted straight or branched chain alkyl, alkenyl, or alkynyl group; aryl, aralkyl; cycloalkyl; or a heteroaryl or heteroaralkyl group. These groups can be unsubstituted or can be substituted by radicals such as OH, SH, SR (R is alkyl or aryl), alkyl, alkoxy, halo, cyano, carboxy, sulfamino, carbamoyl, sulfonyl, azido, amino, substituted amino, haloalkyl, carboxyalkyl, carbamoylalkyl, N-substituted carbamoylalkyl, guanidino, N-substituted guanidino, guanidinoalkyl, and the like. Representative examples of such acyl groups that might be mentioned are those wherein R" is benzyl, p-hydroxybenzyl, 4-amino-4-carboxybuthyl, methyl, cyanomethyl, 2-pentenyl, n-amyl, n-heptyl, ethyl, 3- or 4-nitrobenzyl, phenethyl, β,β-dipenhylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)-5-methyl-4-isoxazolyl, D-4-amino-4-carboxybutyl, D-4-N-benzoylamino-4-carboxy-n-butyl, p-aminobenzyl, o-aminobenzyl, m-aminobenzyl, (3-pyridyl)methyl, 2-ethoxy-1-napthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-quanidinophenyl)-4-isoxazolyl, 4-guanidinomethylphenyl, 4- guanidinomethylbenzyl, 4-guanidinobenzyl, 4-guanidinophenyl, 2,6-dimethoxy-4-guanidinophenyl, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, 4-pyridylmethyl, 5-isoxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)methyl, 2- or 3-(5-methylthienyl)methyl, 2- or 3-(5-methoxythienyl)methyl, 2- or 3-(4-chlorothienyl)-methyl, 2- or 3-(5-sulfothienyl)methyl, 2- or 3-(5-carboxythienyl)methyl, 3-(1,2,5-thiadiazolyl)-methyl, 3-(4-methoxy-1,2,5-thiadiazolyl)methyl, 2-furylmethyl, 2-(5-nitrofuryl)methyl, 3-furylmethyl, 2-thienylmethyl, 3-thienylmethyl, and tetrazolylmethyl.

The acyl group can also be a radical of the formula

wherein $n$ is 0-4, Z represents oxygen, sulfur, or nitrogen and R'' is defined as above. Representative members of the substituent

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)phenylthiomethyl, 2-thiazolylthiomethyl, p-(sulfo)phenxoymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio.

Alternatively, the acyl group can be a radical of the formula

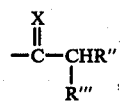

wherein R'' is deined as above and R''' is a radical such as amino, hydroxy, azido, carbamoyl, guanidino, acyloxy, halo, sulfamino, tetrazol, sulfo, carboxy, carbalkoxy, and the like.

Also of interest is the following acyl moiety:

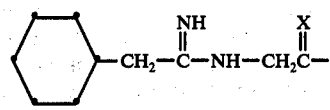

Representative members of the substituent

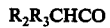

that might be mentioned are α-aminobenzyl, 2-thienylaminomethyl, α-methylaminobenzyl, α-amino-methylmercaptopropyl, α-amino-3 or 4-chlorobenzyl, α-amino-3 or 4-hydroxybenzyl, α-amino-2,4-dichlorobenzyl, α-amino-3,4-dichlorobenzyl, β(—)-α-hydroxybenzyl, α-carboxybenzyl, 3-thienyl-aminomethyl D-(—)-α-amino-3-chloro-4-hydroxybenzyl, D(—)-3-thienylaminomethyl or 1-aminocyclohexyl, α-(5-tetrazolyl)-benzyl, 2-thienyl-carboxymethyl, 3-thineylcarboxy-methyl, 2-furylcarboxymethyl, 3-furyl-carboxymethyl, α-sulfaminobenzyl, 3-thienyl-sulfaminomethyl, α-(N-methylsulfamino)-benzyl, D(—)-2-thienyl-guanidinomethyl, D(—)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl(-hydroxymethyl, 4-(5-chlorothienyl)aminomethyl, 2-(5-chlorothienyl)-hydroxymethyl, 2-(5-chlorothienyl)-carboxymethyl, 3-(1,2-thiazolyl)-aminomethyl, 3-(1,2-thiazolyl)-hydroxymethyl, 3-(1,2-thiazolyl)carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, α-posphonobenzyl, α-diethylphosphono, and α-monoethylphosphono.

The acyl substituents of the general formula $$R_2R_3CHCO$$

wherein $R_2$ and $R_3$ are as defined below represent a preferred group of substituents because of their generally useful antibiotic activity. $R_3$ represents hydrogen, halo, amino, guanidino, phosphono, hydroxy, tetrazolyl, carboxy, sulfo, or sulfamino. $R_3$ represents phenyl, substituted phenyl, a monocyclic heterocyclic 5- or 6-membered ring containing one or more oxygen, sulfur or nitrogen atoms in the ring, such as furyl, thienyl, thiazolyl, isothiazolyl, tetrazolyl, oxadiazolyl, thiadiazolyl and the like, substituted heterocycles, phenylthio, phenyloxy, lower alkyl of 1-6 carbon atoms, heterocyclic or substituted heterocyclic thio groups; or cyano. The substituents can be halo, carboxymethyl, guanidino, guanidinomethyl, carboxamidomethyl, aminomethyl, nitro, methoxy, or methyl.

Particularly preferred are acyl groups where $R_2$ is hydrogen, hydroxy, amino or carboxy and $R_3$ is phenyl, or a 5- or 6-membered heterocyclic ring having one or two sulfur, oxygen or nitrogen hetero atoms, such as tetrazolyl, thienyl, furyl and phenyl.

Examples of acyl radicals of interest are phenylacetyl, 3-bromophenylacetyl, p-aminomethylphenylacetyl, 4-carboxymethylphenylacetyl, 4-carboxyamidomethylphenylacetyl, 2-furylacetyl, 5-nitrofurylacetyl, 3-furylacetyl, 2-thineylacetyl, 5-chlorothienylacetyl, 5-methoxythienylacetyl, α-guanidino-2-thineylacetyl, 3-thineylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-thiadiazolyl-4-acetyl, 3-methyl-1,2,5-thiadiazolyl-4-acetyl, 3-chloro-1,2,5- thiadiazolyl-4-acetyl, 3-methoxy-1,2,5-thiadiazolyl-4-acetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 3-thinylglycyl, phenylmalonyl, 3-chlorophenylmalonyl, 2-thienylmalonyl, 3-thienylmalonyl, α-phosphonophenylacetyl, α-amino cyclohexadieneacetyl, α-sulfaminophenylacetyl, α-hydroxyphenylacetyl, α-tetrazolylphenylacetyl and α-sulfophenylacetyl.

However, it is to be understood that any acyl radical that is conventionally employed in the cephalosporin and penicillin antibiotic art may be employed in the practice of the invention and is to be considered within the scope of the invention.

$R^6$ is $COXR^8$, wherein X is oxygen or sulfur and $R^8$ can be hydrogen or alkyl having 1-10 carbon atoms, straight or branched, such as methyl, ethyl, t-butyl, pentyl, decyl, etc.; substituted alkyl, wherein the alkyl portion has 1-10 carbon atoms but is preferably methyl or ethyl; and the substituent can be a heterocyclic structure having 1-3 hetero atoms of either O, N, or S; such as phthalimidomethyl, succinimidomethyl, phenacyl, p-bromophenacyl, (2-thienyl)methyl, (6-indenyl)-methyl, acetoxyacetylmethyl, carboxymethyl, ethoxyethoxyethyl, (2-methylamino)ethyl, (2-diethylamino)ethyl, 2-(p-methylphenyl)sulfonylethyl, 2-(p-methylphenyl)ethyl, (2-acetamido)ethyl, etc. The substituent on the alkyl group can also be carboxyl, e.g., $R^8$ is α-carboxy-β,β-dimethylpropyl; alkoxyalkyl wherein the alkoxy portion has 1-10 and preferably 1-6 carbon atoms, but can be branched, straight, or cyclic, and the alkyl portion has 1-6 carbon atoms, such as methoxymethyl, ethoxymethyl, isopropoxymethyl, decyloxymethyl, ethoxypropyl, decyloxypentyl, cyclohexyloxymethyl, etc.; alkanoyloxyalkyl wherein the alkanoyloxy portion is straight or branched and has 1-6 carbon atoms and the alkyl portion has 1-6 carbon atoms, such as acetoxymethyl, pivaloyloxymethyl, acetoxyethyl, propionyloxyethyl, acetoxypropyl, etc.; haloalkyl wherein halo is chloro, bromo, fluoro, or iodo, and the alkyl portion is straight or branched having 1-6 carbon atoms, e.g., 2,2,2-trichloroethyl, trifluoroethyl, 2-bromopropyl, diiodomethyl, 2-chloroethyl, 2-bromoethyl, etc.; alkenyl having 1-10 carbon atoms, either straight or branched, e.g., allyl, 2-propenyl, 3-butenyl, 4-pentenyl, 2-butenyl, 3-pentenyl, 3-methyl-3-butenyl, methallyl, etc.; alkynyl having 1-10 carbon atoms, either straight or branched, e.g., 3-pentynyl, propargyl, ethynyl, etc.; alkanoyl, either straight or branched, having 1-10 carbon atoms, such as pivaloyl, acetyl, propionyl, etc.; aralkyl wherein alkyl has 1-3 carbon atoms, such as benzyl, benzhydryl, and substituted benzyl or benzylhydryl, e.g., p-pivaloyloxybenzyl, p-t-butyl-benzyl, m-phenylbenzyl, o-nitrobenzyl, 3,4-dinitrobenzyl, p-methoxybenzyl, p-nitrobenzyl, 3,5-dichloro-4-hydroxybenzyl, p-methoxybenzhydryl, p-carboxybenzyl, the latter being either the free acid or the sodium salt, 2,4,6-trimethylbenzyl, p-(sodium-carboxylate)benzyl, p-methylbenzyl, or phenylethyl, 2-(p-methylphenyl)ethyl, and the arylthioalkyl analogues; aryloxyalkyl wherein aryl is preferably a phenyl ring having 0-3 substituents, preferably 0 or 1 substituents in the ortho or para positions and alkyl is 1-6 carbon atoms, e.g., (4-methoxy)phenoxymethyl, phenoxymethyl, (4-chloro)phenoxymethyl, (4-nitro)phenoxymethyl, (4-benzyloxy)phenoxymethyl, (4-methyl)-phenoxymethyl, (4-benzyloxy)phenoxymethyl, (4-methyl)phenoxymethyl, (2-methoxy)phenoxymethyl, (1-phenoxy)ethyl, (4-amino)phenoxymethyl, (4-methoxy)phenylthiomethyl, (4-chloro)phenylthiomethyl, phenylthioethyl; aryl wherein aryl is phenyl or substituted phenyl having 0-3 substituents, preferably 0 or 1 substituent in the ortho or para position, e.g., (4-methyl)phenyl, (4-hydroxy)phenyl; aralkenyl wherein aryl is phenyl and alkenyl has 1-6 carbon atoms, such as 3-phenyl-2-propenyl; aralkoxyalkyl wherein aralkoxy is benzyloxy, and alkyl has 1-3 carbon atoms, such as benzyloxymethyl, (4-nitro)benzyloxymethyl, (4-chloro)-benzyloxymethyl; alkylthioalkyl wherein the alkylthio portion has 1-10 and preferably 1-6 carbon atoms, but can be branched, straight, or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl, etc., or monocyclic aryl wherein aryl is phenyl, or substituted phenyl such as p-nitrophenyl, 3,5-dinitrophenyl, or p-carboxyphenyl, the latter having either the free acid or the sodium salt form.

In addition to the esters listed above, amides can also be employed, i.e., wherein X is the

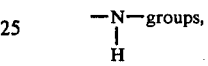

and $R^8$ is as defined.

Particularly preferred esters are those in formula I wherein X is oxygen and $R^8$ is aralkyl, aryloxyalkyl, aralkoxyalkyl, alkylthioalkyl, haloalkyl, or alkenyl.

It will be apparent from a further reading of this application that in many of the chemical reactions described, the cephalosporin is blocked at position 4 by a so-called "easily removable blocking group". Many of these groups are contained within the above definition of the chain —$COXR^8$ in formula I. However, we have found it more convenient to use only relatively a few of these groups during such chemical reactions, then to remove the group to the free acid, and subsequently to react the latter with the desired alcohol to yield the suitable ester.

In this connection, it is noted that preferred "blocking groups" include the sub-generic groups defined above as aralkyl, haloalkyl, alkanoyloxyalkyl, alkoxyalkyl, alkenyl, substituted alkyl, or aralkoxyalkyl, and also include mono, di and trialkylsilyl wherein alkyl has 1-10 carbon atoms.

More specifically, preferred "blocking groups" include benzyl, p-nitro phenacyl, methoxymethyl, trichloroethyl, trimethylsilyl, benzoylmethyl, p-bromophenacyl, p-nitrobenzyl, p-bromophenyl, p-methoxybenzyl, benzhydryl. These blocking groups are preferred since they are generally recognized easily-removable blocking groups in cephalosporin and penicillin art. Although we describe procedures for the removal of these blocking groups, such processes are considered within the skill of those in the art.

On the other hand, the novel cephalosporins of this invention are best utilized pharmacologically as either the free acid in the form of commonly used, non-toxic pharmaceutically acceptable salts, or certain of the above listed esters. For instance, esters belonging to the groups defined as aralkyl, alkylthioalkyl, or alkenyl yield final products having oral activity. More specifically, high oral activity of the novel cephalosporins is obtained when $R^8$ is 2-methylthioethyl, pivaloxymethyl, p-pivalyloxybenzyl, benzyl, or 3-buten-1-yl.

By the term "non-toxic pharmaceutically acceptable salts" is meant salts that are suitable for isolating, purifying and/or marking purposes, for example salts with bases or with acids, as well as inner salts. Salts with bases are in the first place metal salts, especially alkali metal salts, for example sodium or potassium salts, or alkaline earth metal salts, for example magnesium or calcium salts, or ammonium salts, including ammonium salts with organic bases such as tri-lower alkyl-amine, for example trimethylamine or triethylamine, or N-lower alkylazacycloalkanes, for example 1-methyl-pyrrolidine or 1-ethyl-piperidine, also dibenzylethylenediamine or procaine. They are obtained, for example, by treating the free compounds or inner salts with the basic compounds, as desired with the aid of an ion exchange resin.

Acid addition salts are in the first place those with strong inorganic acids, such as hydrochloric, hydrobromic or sulphuric acid, or with strong organic acids such as strong organic sulphonic acids, for example methanesulphonic, 2-hydroxyethanesulphonic or p-toluenesulphonic acid, or with a strong organic carboxylic acid, for example trifluoroacetic acid. They can be obtained, for example, by treating the free compounds with the appropriate strong acids if desired with the aid of an ion exchange resin.

Inner salts, which appear as hybrid ions, are obtained by treating an acid addition salt with an appropriate, weakly basic ion exchange resin, or by titrating with a base up to the isoelectric point, or from a salt with a base by treatment with acid.

The most preferred embodiments of the present invention are those having the following structure:

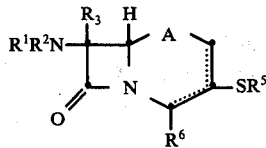

wherein
A is S, O, or $CH_2$;
$R^1$, $R^2$ and $R^6$ are as previously defined;
$R^3$ is selected from the group consisting of H, $OCH_3$ and lower alkylthio having from 1 to 6 carbon atoms;
$R^5$ is selected from the group consisting of hydrogen, lower alkyl having 1 to 6 carbon atoms, substituted phenyl, N-methyltetrazolyl, amino alkyl such as β-aminoethyl, β-dimethylaminoethyl, β-thioethyl, β-hydroxyethyl, β-carboxyethyl, and 2-methyl-1,3,4-thiadiazolyl-5yl.

The novel 3-substituted thio cephalosporins (and nuclear analogues thereof) of the present invention are conveniently prepared by the following reation:

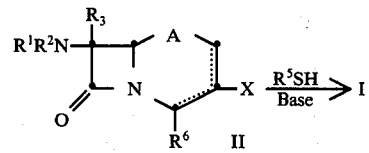

wherein X is a leaving group selected from the group consisting of halogen, such as chloro, bromo or iodo, and $OSO_2R$ is alkyl or aralkyl such as, p- toluenesulfonic acid, trifluoromethylsulfonic acid, and methanesulfonic acid.

In words relative to the above reaction, the 3-substituted cephalosporin reactant (II) is treated with the thiol of choice, $R^5SH$, in the presence of base. Suitable bases may be selected from tertiary amines and inorganic bases such as triethylamine, pyridine, sodium hydride, phenyl lithium and the like. Suitable solvents for the reaction include, representatively, $CH_2Cl_2$, $CHCl_3$, tetrahydrofuran (THF), $CH_3CN$, dimethylformamide (DMF) benzene, acetone. and the like. Typically the reaction is conducted at a temperature of from about 0° C. to reflux for from a few minutes to 18 hours.

Suitable starting material (II) are known in the art. See for example *J. Chem. Soc. Chem. Comm.*, 1972, 800; Tetrahedron Letters 1972, 2341 and 3241 (Ochiai, et al.; *J.A.C.S.* 96 4986 (1974) (Chauvette, et al.); and *Helv.* 57 1919 (1974) (Chauvette, et al.); and *Helv.* 57 1919 (1974) (Scartazzini), which references are incorporated herein by reference. Basically, the starting materials are conveniently prepared according to the following reaction scheme:

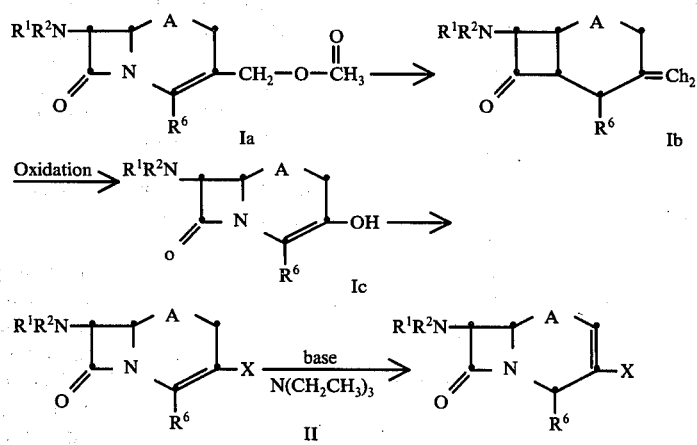

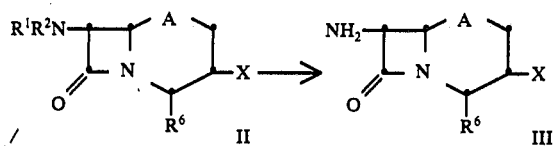

In words relative to the above diagram, the 3-methylidene species, Ib, is obtained from the 3-acetoxymethyl species, Ia, by reduction with $Cr(OAc)_2$, electrolytic reduction, or displacement of OAc by

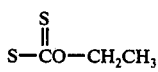

and Raney Nickel desulfurization of the product. Such procedures are known in the art. Oxidation of Ib with, for example with ozone, provides the 3-hydroxyl species, Ic. Typically the oxidation is conducted in solvents such as $CH_2Cl_2$, ethylacetate, and the like at a temperature of from $-78°$ to $25°$ C. for from a few minutes to 2 hours. The resulting 3-hydroxy species is converted to the desired 3-X species (II) by, depending upon the identity of X desired, reacting it with the appropriate reagent: When X is chloro, an appropriate reagent is thionylchloride; when X is bromo, an appropriate reagent is thionylbromide; when X is iodo, an appropriate reagent is $(C_4H_9)_4N^+I^-$, on the chloro compound; when X is $RSO_2O$, appropriate reagents are tosyl chloride, methane sulfonyl chloride, and $(CF_3CO)_2O$. Suitable solvents for this reaction step are DMF, $CHCl_2$, chloroform, pyridine and the like; typically the reaction is conducted at from about $-10°$ C. to reflux for from a few minutes to 18 hours. Primal intermediate III, is obtained from II ($R^1$ and $R^2$ are not both hydrogen) by treatment with $PCl_5$ to give the imino chloride, which with MeOH gives the imino ether, which is hydrolyzed to the free amine III.

The $\Delta^2$ isomer is obtained from the $\Delta^3$ isomer by treatment with a base such as $Et_3N$, diisopropyl ethyl amine, in $CHCl_3$, or $CH_2Cl_2$ as solvent.

It is to be noted that the above reaction scheme is regio-specific for the 3-position and that there are no criticalities of reaction parameters other than those set forth above and elaborated upon in the following examples.

The present invention embraces all stereoisomers of the compounds prepared by the above process. However, it is well-known in the bicyclic β-lactam art that certain isomers of a given species are more active than their corresponding enantiomorph. This appears to be true for the instant invention. While the extent of this relationship of antibiotic activity to configuration cannot be stated for all species embraced by the present invention, it is believed that the cis isomers (relative to asymmetric carbons 6 and 7) are more active. Such isomers may be depicted by the following projection formula:

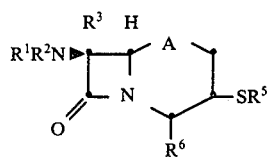

Pharmaceutically acceptable salts which may be formed using procedures well known to the art from the compounds of the invention include (a) inorganic base salts such as alkali metal, e.g. sodium and potassium, alkaline earth e.g. calcium, and organic base salts, e.g. procaine and dibenzylethylene diamine salts and (b) acid addition salts e.g. with hydrochloric, hydrobromic, sulphuric, nitric, phosphoric, toluene-p-sulphonic and methanesulphonic acids. In addition to salts, the novel compounds of the present invention may be administered in the form of esters, including those discussed above. Examples of esters that might be mentioned are esters of alcohols, phenols, mercaptans, and thiophenols of the general formula $-COXR^8$ wherein $R^8$ represents the radical of an alcohol or a thiol such as methyl, ethyl, tertiary butyl, a substituted alkyl such as phthalimidomethyl, succinimidomethyl, phenacyl, a substituted phenacyl for example p-bromophenacyl, a β-substituted ethyl group such as 2,2,2-trichloroethyl, 2-(p-methylphenyl)ethyl, 2-(p-methylphenyl)sulfonylethyl, 2-methylaminoethyl, methylthioethyl, 2-chloro(or bromo)ethyl, benzyl, a substituted benzyl group such as p-nitrobenzyl, m-phenoxybenzyl, p-pivaloyloxybenzyl, benzyloxybenzyl, p-t-butylbenzyl, p-methoxybenzyl, 3,5-dinitrobenzyl, 2,4,6-trimethylbenzyl, 3,5-dichloro-4-hydroxybenzyl, and the like, a benzhydryl or substituted benzhydryl group such as p-methoxybenzhydryl an acyloxyl alkyl group such as acetoxymethyl, pivaloyloxymethyl, or ethyl, an alkoxy group such as methoxymethyl, aryloxymethyl such as phenoxymethyl, or a monocyclic aryl group for example phenyl or substituted phenyl such as p-nitrophenyl or 3,5-dinitrophenyl or unsaturated alkyl such as 3-methylbutenyl, methallyl, 3-butenyl, and the like. These esters are readily prepared in accordance with processes well known in the art.

The novel compound are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus* (penicillin resistant), *Escherichia coli*, *Klebsiella pneumoniae*, *Salmonella typhosa*, *Pseudomonas aeriginosa* and *Bacterium proteus*. The compounds of the present invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in water-based paints and in the white water of paper mills to inhibit the growth of harmful bacteria.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions may be presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicle before use. Such liquid preparations may contain conventional additive such as suspending agents, for example, sorbitol syrup, methyl cellulose, glucose/sugar syrup, gelatin, hydroxyethylcellulose, carboxymethyl cellulose aluminum stearate gel or hydrogenated edible fats, emulsifying agents, for example lecithin, sorbitan monooleate or acacia; non-aqueous vehicles, which may include dible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being teated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight. The preferred daily dosage for the compounds of the invention range from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. by weight of active ingredient based upon the total weight of the composition; however, in general, it is preferable to employ a dosage amount in the range of from about 250 to 1000 mg. In parenteral administration the unit dosage is usually the pure compound in a slightly acidified sterile water solution or in the form of a soluble powder intended for solution. Typical formulations of specific products are described below.

EXAMPLE 1

Preparation of benzhydryl-7,β-phenylacetamido-1-methylenedethia-3-chloro-3-cephem-4-carboxylate and the corresponding 7-amino species, $R^1=R^2=H$

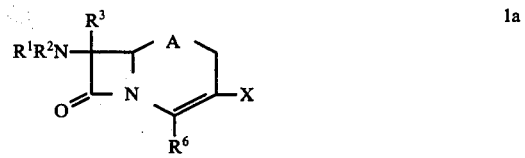

1a $R^2 = H$
$R^1 =$

$R^3 = H$
$A = CH_2$
$X = Cl$
$R^6 = COOCH(C_6H_5)_2$

Step A

Sodium 7β-phenylacetamido-1-methylenedethiacephalosporanate (3.70 g.) is dissolved in 100 ml DMSO and added to 4.5 g chromous acetate under $N_2$. The reaction mixture is stirred overnight at 25° C. The reaction mixture is diluted with water, and extracted with ethyl acetate. The aqueous phase is acidified to pH 2 and extracted with etylacetate. The ethylacetate extract is dried and evaporated to give 7,β-phenylacetamido-1-methylenedethia-3-methylenecepham-4-carboxylic acid.

Step B

7,β-Phenylacetamido-1-methylenedethia-3-methylenecepham-4-carboxylic acid (3.06 g.) is dissolved in 30 ml. ethylacetate and treated with 2.0 g. of dipenhyldiazomethane. The reaction mixture is allowed to stand overnight at 25° C., and then the solvent is removed under reduced pressure. The residue is chromatogrammed on silica gel to give benzhydryl 7,β-phenylacetamido-1-methylenedethia-3-methylenecepham-4-carboxyhlate.

Step C

Benzhydryl 7,β-phenylacetamido-1-methylenedethia-3-methylene-cepham-4-carboxylate (4.6 g.) is dissolved in 500 ml. of $CH_2Cl_2$, cooled to −78° and treated with a stream of ozone in oxygen until a blue color persists in the reaction mixture. After 1 minute at −78° the reaction mixture is treated with 5 ml. of dimethyl sulfide and the reaction mixture is allowed to stand at −78° for 20 min. followed by 1 hour at 25° C. The solvent is removed under reduced pressure to give the crude benzhydryl 7,β-phenylacetamido-1-methylenedethia-3-hydroxy-3-cephem-4-carboxylate.

Step D

The crude product from the ozonolysis (3.0 g.) is dissolved in 60 ml. DMF cooled to 0° and treated with 1.5 ml. $SOCl_2$. The reaction mixture is diluted with ice cold pH 7 buffer and the crude product precipitates out. This is separated from the aqueous phase and taken up in methylene chloride, dried over $MgSO_4$ and evaporated. The residue is chromatogrammed on silica gel to give benzhydryl 7,β-phenylacetamido-1-methylenedethia-3-chloro-3-cephem-4-carboxylate.

Step E

Benzhydryl 7,β-phenylacetamido-1-methylenedethia-3-chloro-3-cephem-4-carboxylate (1.0 g.) is dissolved in 20 ml. of dry methylene chloride cooled to 0°. 1 Ml. pyridine is added and then a solution of 0.5 g. $PCl_5$ in 5 ml. of $CH_2Cl_2$ is added. The reaction mixture is stirred at 0° for 1 hour and then treated with methanol (5 ml.). After 6 hours at 25° C., 5 ml. of 5% aqueous phosphoric acid is added and the reaction mixture is stirred vigorously for 40 minutes. The reaction mixture is made basic and extracted with methylene chloride. The $CH_2Cl_2$ extract is dried and evaporated. The residue on chromatography on silica gel gives benzhydryl 7-amino-1-methylenedethia-3-chloro-3-cephem-4-carboxylate.

The following table illustrates the preparation of representative species which are analogous to those prepared in Example 1, structure Ia; exception to established procedure are indicated were necessary.

Ia $R^1R^2N$—[structure with $R^3$, A, N, $R^6$, X]

| Compound | $R^1$ | $R^2$ | $R^3$ | A | $R^6$ | X |
|---|---|---|---|---|---|---|
| 1 | H | H | H | $CH_2$ | COOH | Cl |
| 2 | H | H | H | S | COOH | Cl |
| 3 | H | H | H | O | COOH | Cl |
| 4 | H | H | H | NH | $CO_2TMS$ TMS=trimethylsilyl | BR |
| 5 | $C_6H_5$—$CH_2C$(=O) | H | H | $CH_2$ | $COOCH(C_6H_5)_2$ | Cl |
| 6 | [thiophene]—$CH_2C$(=O) | H | H | $CH_2$ | $COOCH(C_6H_2)_2$ | Cl |
| 7 | $C_6H_5CH(OH)$—C(=O) | H | H | $CH_2$ | $COOCH_2$—$C_6H_4$—$NO_2$ | Cl |
| 8 | $C_6H_5$—CH(COOH)—C(=O) | H | H | $CH_2$ | COOH | Cl |
| 9 | $C_6H_5$—CH($NH_2$)—C(=O) | H | H | $CH_2$ | $COOCH(C_6H_5)_2$ | Cl |
| 10 | $C_6H_5CH_2C$(=O) | H | H | S | $COOCH_2$—$C_6H_4$—$NO_2$ | Cl |
| 11 | $C_6H_5$—CH(OH)—C(=O) | H | H | S | $COOCH(C_6H_5)_2$ | Cl |
| 12 | $C_6H_5$—CH(COOH)—C(=O) | H | H | S | COOH | Cl |
| 13 | [thiophene]—$CH_2$—C(=O) | H | H | O | $COOCH_2C_6H_5$ | Cl |

-continued

| Compound | R¹ | R² | R³ A | R⁶ | X |
|---|---|---|---|---|---|
| 14 | (furan-CH₂-C(=O)-) | H | H O | COOCH₂C₆H₅ | Cl |
| 15 | C₆H₅—CH(NH₂)—C(=O)— | H | H O | COOCH(C₆H₅)₂ | Cl |
| 16 | C₆H₅—CH₂—C(=O)— | H | H NH | COOCH(C₆H₅)₂ | Cl |

EXAMPLE 2

Preparation of
3-(2-Aminoethylthio)-7,β-phenylacetamido-3-cephem-4-carboxylic acid

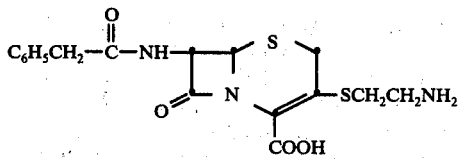

Step A: Trimethylsilyl 3-chloro-7,β-phenylacetamido-3-cephem-4-carboxylate

3-Chloro-7,β-phenylacetamido-3-cephem-4-carboxylic acid (0.105 g.) is suspended in 2 ml. dry $CH_2Cl_2$ under nitrogen. Triethylamine (0.042 ml.) (1 eq) is added to make the triethylamine salt and the solution is treated with 0.048 g. (1.5 eq) of trimethylsilyl chloride. The reaction mixture is stirred at 25° C. for 0.5 hour and the solvent and excess reagent are evaporated under reduced pressure to give the trimethylsilyl ester of 3-chloro-7,β-phenylacetamido-3-cephem-4-carboxylic acid.

Step C: Trimethylsilyl 3-(2-aminoethylthio)-7,β-phenyl acetamido-3-cephem-4-carboxylate Trimethylsilyl-3-chloro-7,β-phenylacetamido-3-cephem-4-carboxylate from above is dissolved in 1 ml. anhydrous $CH_2Cl_2$ and 1 ml. anhydrous THF under $N_2$ and the solution is treated with 0.050 g. (1.5 eq) of 2-aminoethanethiol hydrochloride and 0.080 ml. of triethylamine (2.5 eq) is added dropwise over 1 minute. The reaction mixture is tirred at 25° C. under nitrogen for 2 hours to give a solution of trimethylsilyl-3-(2-aminoethylthio)-7,β-phenylacetamido-3-cephem-4-carboxylate. U.v: $\lambda_{max}^{CH_2Cl}$ 306 mμ. Evaporation of the solvents under reduced pressure gives a residue which is the above-metnioned ester.

Step D: 3-(2-Aminoethylthio)-7,β-phenylacetamido-3-cephem-4-carboxylic acid

The trimethylsilyl ester from above is treated with 2 ml. of 0.25 molar pH 7 phosphate buffer. A gum is formed which on further stirring gives a solid which is filtered off and washed with water and dried to give 0.046 g. of 3-(2-aminoethylthio)-7,β-phenylacetamido-3-cephem-4-carboxylic acid. U.v. $\lambda_{max}^{H_2O}$ 282 mμ.

E=7100; i.r. (μ); 3.1 (NH), 5.65 (β-lactam), 5.9 (broad, amide and carboxylate), 6.5 (amide II). M.s. (high resolution) M⁺ 609.1998 (for trisilyl derivative). Calc. for $C_{17}H_{19}N_3O_4S_2$ + 3 trimethylsilyl = 609.1996.

EXAMPLE 3

3-(2-Aminoethylthio)-7,β-Phenylacetamido-3-Cephem-4-Carboxylic Acid via the corresponding p-Nitrobenzyl-4-carboxylate Step A: p-Nitrobenzyl-3-(2-aminoethylthio)-7,β-phenylacetamido-3-cephem-4-carboxylate p-Nitrobenzyl-3-chloro-7,β-phenylacetamido-3-cephem-4-carboxylate (0.100 g.) is dissolved in 2 ml. anhydrous $CH_2Cl_2$ and 2 ml. anhydrous THF; 0.024 g. of 2-aminoethanethiol hydrochloride, followed by 0.056 ml. of triethylamine are added. The mixture is stirred at 25° C. for 2.5 hours. The reaction mixture is washed once with water, dried and evaporated to give 0.104 g. of crude product which is purified by preparative tlc on silica gel using 25% EtOAc/$C_6H_6$ as eluant. Yield 0.022 g. i.r (μ): 3.1 (NH), 5.66 (β-lactam), 6.0 (broad, ester and amide), 6.23 (nitro). U.v. $\lambda_{max}^{CH_2Cl_2}$ 306mμ (E = 11,500). nmr δ: 1.8 є 2.4 ($NO_2$-$C_6\underline{H}_4$—); 2.66 ($C_6\underline{H}_5$); 3.3 d (J = 8 cp.s. N$\underline{H}$—C=O); 4.6 q (J = 4.5, J = 8, C - 7H); 4.75 q, ($C\underline{H}_2$—$C_6H_4NO_2$); 4.93 d (J = 4.5, C-6 H); 6.33, s ($C_6H_5C\underline{H}_2$) 6.4–7.8 m (C-2 H and S—$C\underline{H}_2C-\underline{H}_2$—N$\underline{H}_2$).

Step B: 3-(2-Aminoethylthio)-7,β-Phenylacetamido-3-cephem-4-carboxylic acid p-Nitrobenzyl-3-aminoethylthio-7,β-phenylacetamido-3-cephem-4-carboxylate (0.020 g.) is dissolved in 1 ml. dioxane and 1 ml. $H_2O$; 0.020 g. of 10% pd/C is added and the mixture hydrogenolyzed at 40 lbs $H_2$ pressure for 1 hour. The catalyst is filtered off and washed with water. The filtrate and washings are extracted with EtOAc and the aqueous phase is freeze-dried to give the product.

EXAMPLE 4

Preparation of
3-(2-Dimethylaminoethylthio)-7,β-phenylacetamido-3-cephem-4-carboxylic acid Step A: Benzhydryl 3-chloro-7,β-phenylacetamido-3-cephem-4-carboxylate 3-Chloro-7,β-phenylacetamido-3-cephem-4-carboxylic acid (0.352 g) is dissolved in 5 ml. ethyl acetate and treated with 0.200 g. of dipehnyldiazomethane and the reaction mixture allowed to stand for 4 hours at 25° C. The solvent is evaporated and the residue is chromatographed on silica gel to give benzhydryl 3-chloro-7,β-phenylacetamido-3-cephem-4-carboxylate.

I.R. μ: 3.02 (NH); 5.60 (β-lactam); 5.78 (ester) 5.91 (amide).

Step B: Benzhydryl-3(2-dimethylaminoethylthio)-7,β-phenylacetamido-3-cephem-4-carboxylate Benzhydryl-3-chloro-7,β-phenylacetamido-3-cephemcarboxylate (0.050 g.) is dissolved in 1 ml. CH₂Cl₂ and 1 ml THF. Dimethylaminoethanethiol hydrochloride (0.014 g.) is added, followed by 0.013 ml. of triethylamine. The reaction mixture is stirred at 25° C. for 2.5 hours, then diluted with CH₂Cl₂ and washed with water. The organic phase is dried and evaporated. The residue on preparative tlc on silica gel gives 0.020 g. of product which is contaminated with its Δ² isomer.

I.R. μ: 3.05 (NH); 3.62

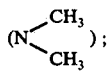

5.6 (β-lactam); 5.71 (ester); 5.95 (amide).
N.M.R. δ: 7.3, s (C₆H₅); 6.82 (CH(C₆H₅)₂); 4.9–6.0, m (β-lactam protons); 3.6 (C₆H₅CH₂); 3.46, ν (C-2 protons); 2.6, m (S—CH₂—CH₂—N); 2.13

M.S. M⁺587.

Step C: 3-(2-Dimethylaminoethylthio)-7,β-phenylacetamido-3-cephem-4-carboxylic acid Benzhydryl-3-dimethylaminoethylthio-7,β-phenylacetamido-3-cephem-4-carboxylate (0.035 g.) (mixture with Δ² isomer) is dissolved in 0.2 ml. anisole, cooled to 0° and treated with 1 ml. TFA at 0°. The mixture is allowed to stand 2 minutes at 0° and then diluted with C₆H₆ and evaporated. The residue is partitioned between ether and water. The aqueous phase is taken to pH 7 and freeze-dried. The residue is chromatographed by high pressure liquid chromatography, using a Waters' Associate C₁₈ Bondapak column and 10% THF in H₂O eluant. The product (0.005 g.) is obtained free of the Δ² isomer.

U.V. λ$_{max}^{H_2O}$ 2,84, E = 6500.
N.M.R. δ: 7.35 (C₆H₅); 5.56, d (C-7H); 5.15, d (C-6H); 3.68, s (C₆H₅CH₂); 3.55, ν (C-2H); 3.2, m (S—CH₂CH₂N); 2.85, s (N—CH₃)
M.S M⁺493 monosilyl derivative.

EXAMPLE 5

Preparation of 3-(2-Dimethylaminoethylthio)-7,β-(D-mandelylamido)-3-cephem-4-carboxylic acid Step A: 7,β-(D-O-formylmandelylamido)-3-methylenecepham-4-carboxylic acid 7-Amino-3-methylenecepham-4-carboxylic acid (2.14 g.) is dissolved in 20 ml. of H₂O and 20 ml. acetone and treated with 1.68 g. of NaHCO₃. The reaction mixture is cooled to 0° C. and treated with D-O-formylmandelyl chloride (2.1 g.) in 10 ml. acetone, added dropwise over 15 minutes. The reaction mixture is stirred at 0° for ½ hour and then allowed to warm to 25° C. and stirred for 1 hour. The reaction mixture is diluted with water, adjusted to pH 7 with 5% NaHCO₃ and extracted with ethyl acetate. The aqueous phase is taken to pH 2 and extracted with ethyl acetate. The ethyl acetate extract is dried and evaporated to give the product.

Step B: Benzhydryl 7,β-(D-O-formylmandelylamido)-3-methylenecepham-4-carboxylate The crude acid from above is dissolved in 40 ml. ethyl acetate and treated with 2.5 g. of diphenyldiazomethane. The reaction mixture is allowed to stand at 25° C. overnight. The solvent is removed under reduced pressure and the residue is chromatogrammed on silica gel to give 0.53 g. of product.

I.R. μ: 3.05 (NH); 5.62 (β-lactam); 5.75 (ester); 5.9 (amide).
N.M.R. δ: 8.05 (H—C=O); 7.3, s (C₆H₅); 6.93,

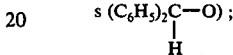

6.2 (O—CH—C=O); 5.56, q (c-7 H); 5.3, d (C-6 H); 5.15, d (C=CH₂); 3.2 q (C-2 H).

Step C: Benzhydryl 7,β-(D-O-formylmandelylamido)-3-chlorocephem-4-carboxylate

Benzhydryl 7,β-(D-O-formylmandelylamido)-3-methylenecepham-4-carboxylate (0.842 g) is dissolved in 100 ml. CH₂Cl₂ cooled to −78° C. and treated with ozone until a blue color persists in the reaction mixture. Dimethylsulfide (1 ml.) is then added and the reaction mixture is maintained at −78° C. for 20 minutes and then 1.5 hours at 25° C. The solvent is removed under reduced pressure to given benzhydryl 7,β-(D-O-formylmandelylamido)-3-oxo-cepham-4-carboxylate, which is dissolved in 20 ml. DMF and cooled to 0° C. Thionyl chloride (0.4 ml.) is added and the mixture is allowed to stir for 45 minutes at 25° C. Water (ice cold) (40 ml.) and pH 7 buffer (10 ml.) is added and the mixture is stirred vigorously. A solid precipitates out which is filtered off, wahsed with a little water, taken up in CH₂Cl₂, dried over MgSO₄ and evaporated. The residue is chromatogrammed on silica gel (30 g.) using 15% EtoAc/C₆H₆ to give 0.230 g of the product.

N.M.R. δ: 8.0,

7.3, s (C₆H₅); 7.0, s ((C₅H₅)₂CH—); 6.2, s (O—CH—C=O); 5.7, g (C-7 H); 4.8, d (C-6H); 3.37, g (C-2H).

Step D: Benzhydryl 7,β-(D-Mandelylamido)-3-(2-dimethylaminoethylthio)-3-cephem-4-carboxylate Benzhydryl 7,β-(D-O-formylmandelylamido)-3-chlorocephem-4-carboxylate (0.050 g) is dissolved in 1 ml. CH₂Cl₂ and 1 ml. THF. 2-Dimethylaminoethanethiol hydrochloride (0.015 g.) is added followed by 0.028 ml. of Et₃N. The reaction mixture is stirred at 25° C. for 1.5 hours under N₂. The reaction mixture is diluted with CH₂Cl₂ washed with water, dried and evaporated. The residue is purified by preparative tlc to give the product (0.018 g) as a mixture of Δ² and Δ³ compounds.

I.R. μ: 3.0 (NH); 3.6

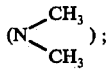

5.6 (β-lactam); 5.69 (ester) 5.9 (amide).
N.M.R. δ: 7.3, s (C₆H₅); 6.9, s (C₆H₅)₂CH—O);
5.0–6.0, m. (β-lactam) and

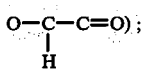

2.8, m (S—CH₂—CH₂—N); 2.15, s (N—CH₃).

Step E: 3-(2-Dimethylaminoethylthio)-7,β-(D-mandelylamido) 3-cephem-4-carboxylate acid Benzhydryl 7,β-(D-mandelylamido)-3-(2-dimethylaminoethylthio)-3-cephem-4-carboxylate (0.025 g.) is dissolved in 0.2 ml. anisole, cooled to 0° C. and treated with 1 ml. of TFA at 0° for 2 minutes. The TFA is removed under reduced pressure, the residue is taken up in 10 ml. C₆H₆ and evaporated under reduced pressure to give a residue which is taken up in Et₂O and H₂O. The aqueous phase is separated, washed once with ether and ajusted to pH 7. with a few drops of 5% NaHCO₃. The solution is freeze-dried. The residue is purified on HPLC using a Waters C-18 Bondpak column and 10% THF/H₂O as eluant to give 0.008 g of the Δ³ product and 0.013 g of the Δ² isomer.

N.M.R. δ: 7.45, s (C₆H₅); 5.54, d (c-7 H); 5.24, s (H—C—OH); 5.15, d (C-6H); 3.55 ν (C-2H); 3.22, m (—S—CH₂—CH₂N); 2.82, s (N—CH₃).

EXAMPLE 6

The following chart illustrates the preparation of representative species of the present invention, prepared by the procedure of the foregoing Examples.

| Compound | R¹ | R² | R³ | A | R⁵ | R |
|---|---|---|---|---|---|---|
| 1 | [thiophene]-CH₂-C(=O)- | H | —OCH₃ | S | —CH₃ | CO₂Na |
| 2 | C₆H₅—CH₂—C(=O)- | H | —OCH₃ | S | —CH₂—CH₂—NH₂ | CO₂H |
| 3 | [thiophene]-CH₂-C(=O)- | H | H | O | —CH₃ | CO₂Na |
| 4 | [thiophene]-CH(CO₂H)-CO- | H | H | O | S—CH₂—CH₂N(CH₃)₂ SCRCRM | CO₂Na |
| 5 | [thiophene]-CH₂-C(=O)- | H | H | CH₂ | —S—CH₂—CH₂N(CH₃)₂ | COOH |
| 6 | C₆H₅—C(OH)—C(=O)- | H | H | CH₂ | —S—CH₂—CH₂—N(CH₂—CH₃)₂ | COOH |
| 7 | C₆H₅—CH(NH₂)—C(=O)- | H | H | CH₂ | —SCH₃ | COOH |
| 8 | [thiophene]-CH₂C(=O)- | H | H | O | —S—CH₂—CH₂—COOH | COONCl |

EXAMPLE 7

Preparation of Pharmaceutical Compositions

One such unit dosage form consists in mixing 120 mg. of pivaloyloxymethyl ester of Compound 1, Example 6, with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| 3-(2-Aminoethylthio)-7,β-phenylace-tamido-3-cephem-4-carboxylic acid | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | | |
|---|---|---|
| Ampoule: | | |
| 3-(2-Aminoethylthio)7,β-phenylace-tamido-3-cephem-4-carboxylic acid | | 500 mg. |
| Diluent: Sterile Water for Injection | | 2 cc. |
| OPTHALMIC SOLUTION | | |
| 3-(2-Aminoethylthio)7,β-phenylace-tamido-3-cephem-4-carboxylic acid | | 100 mg. |
| Hydrooxypropylmethyl Cellulose | | 5 mg. |
| Sterile Water | to | 1 ml. |
| OTIC SOLUTION | | |
| 3-(2-Aminoethylthio)7,β-phenylace-tamido-3-cephem-4-carboxylic acid | | 100 mg. |
| Benzalkonium Chloride | | 0.1 mg. |
| Sterile Water | to | 1 ml. |
| TOPICAL OINTMENT | | |
| 3-(2-Aminoethylthio)7,β-phenylace-tamido-3-cephem-4-carboxylic acid | | 100 mg. |

-continued

| Polyethylene Glycol 4000 U.S.P. | 400 mg. |
|---|---|
| Polyethylene Glycol 400 U.S.P. | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structural formula:

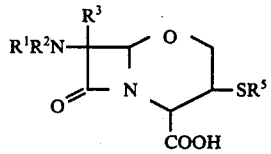

and the non-toxic, pharmaceutically acceptable salts thereof; wherein:

the dotted line indicates provision for both $\Delta^2$ and $\Delta^3$ embodiments;

$R^1$ and $R^2$ are independently selected from the group consisting of hydrogen and acyl;

$R^3$ is hydrogen, methoxy, and lower alkyl thio; and $R^5$ is amino loweralkyl.

2. The $\Delta^3$ compound of claim 1 wherein: $R^5$ is —$CH_2CH_2NH_2$, —$CH_2CH_2N(CH_3)_2$ or —$CH_2CH_2N(CH_2CH_3)_2$.

3. A pharmaceutical composition comprising a therapeutically effective amount, in unitary dosage form, of a compound according to claim 1 and a pharmaceutical carrier therefor.

* * * * *